United States Patent [19]
Mirigian

[11] Patent Number: 5,578,074
[45] Date of Patent: Nov. 26, 1996

[54] IMPLANT DELIVERY METHOD AND ASSEMBLY

[75] Inventor: Gregory E. Mirigian, Fremont, Calif.

[73] Assignee: Target Therapeutics, Inc., Fremont, Calif.

[21] Appl. No.: 363,232

[22] Filed: Dec. 22, 1994

[51] Int. Cl.[6] .................................................. A61F 2/06
[52] U.S. Cl. .................... 623/1; 606/108; 623/12
[58] Field of Search ..................... 623/1, 12; 606/108; 604/95, 107, 114

[56] References Cited

U.S. PATENT DOCUMENTS

| | | |
|---|---|---|
| 3,868,956 | 3/1975 | Alfidi et al. . |
| 4,739,768 | 4/1988 | Engelson . |
| 4,813,934 | 3/1989 | Engelson et al. . |
| 4,884,579 | 12/1989 | Engelson . |
| 4,994,069 | 2/1991 | Ritchart et al. . |
| 5,037,427 | 8/1991 | Harada et al. . |
| 5,055,101 | 10/1991 | McCoy . |
| 5,089,005 | 2/1992 | Harada . |
| 5,108,407 | 4/1992 | Geremia et al. . |
| 5,122,136 | 6/1992 | Guglielmi et al. . |
| 5,143,085 | 9/1992 | Wilson . |
| 5,147,370 | 9/1992 | McNamara et al. . |
| 5,226,911 | 7/1993 | Chee et al. . |
| 5,234,437 | 8/1993 | Sepetka . |
| 5,261,916 | 11/1993 | Engelson . |
| 5,263,964 | 11/1993 | Purdy . |
| 5,290,229 | 3/1991 | Paskar . |
| 5,312,415 | 5/1994 | Palermo . |
| 5,354,295 | 10/1994 | Guglielmi et al. . |

FOREIGN PATENT DOCUMENTS

| | | |
|---|---|---|
| 0145166 | 6/1985 | European Pat. Off. . |
| 2115289 | 9/1983 | United Kingdom . |
| WO92/21400 | 12/1992 | WIPO . |

*Primary Examiner*—Paul B. Prebilic
*Attorney, Agent, or Firm*—Morrison & Foerster

[57] ABSTRACT

A thermally activated occlusive implant delivery assembly is provided. The assembly includes an occlusive implant device and a pusher. The pusher has a distal section and a proximal section. The distal section includes a coupling portion which is shape memory material and exhibits different configurations depending on the coupling portion's temperature. The coupling portion interlockingly engages the implant when it is in one of the configurations and releases the implant from interlocking engagement therewith when in another one of the configurations. In operation, the assembly is introduced into the body of a mammal via a guide catheter suited for the particular lumen being navigated. When the implant is positioned at the desired site, the coupling portion of the pusher is thermally activated to effect the return of its original, pre-set configuration, which is originally formed to release the implant from interlocking engagement therewith. The pusher can then be readily removed from the mammal without imparting any significant force on the implant during retraction.

23 Claims, 2 Drawing Sheets

IMPLANT DELIVERY METHOD AND ASSEMBLY

FIELD OF THE INVENTION

The present invention relates to the delivery of implants in mammals generally, and more particularly to the delivery of occlusive implants, such as embolic coils, utilizing a thermally activated shape memory decoupling mechanism.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in U.S. Pat. Nos. 5,234,437 and 5,261,916, in which methods and devices for delivery of coils or wires within the human body to sites, such as aneurysms, to occlude those sites are disclosed. Coils, such as those discussed in these documents as well as in U.S. Pat. No. 4,994,069, may be of a regular or helical configuration or assume a random convoluted configuration at the site. The coils normally are made of a radiopaque, biocompatible metal such as platinum, gold, tungsten or alloys of these and other metals. In treating aneurysms, it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray techniques and allows a catheter to be navigated through extremely tortuous vessels, even those surrounded by soft tissue such as the brain.

Once the site has been reached, the catheter lumen is cleared by removing the guidewire (if a guidewire has been used), and one or more coils are placed into the proximal open end of the catheter and advanced through the catheter with a pusher. Pushers are wires having distal ends adapted to engage and push the coil through the catheter lumen as a pusher itself is advanced through the catheter. Once the coil reaches the distal end of the catheter, it is discharged from the catheter by the pusher into the vascular site. However, there are concerns when discharging the coil from the distal end of the catheter. For example, the plunging action of the pusher and the coil can make it difficult to position the coil at the site in a controlled manner and with a fine degree of accuracy. Inaccurate placement of the coil can be problematic because once the coil has left the catheter, it is difficult to reposition or retrieve the coil.

Several techniques involving Interlocking Detachable Coils (IDCs), which incorporate mechanical release mechanisms and Guglielmi Detachable Coils (GDCs), which utilize electrolytically actuated release mechanisms, have been developed to enable more accurate placement of coils within a vessel.

One technique for detaching an embolic coil is shown in U.S. Pat. No. 5,261,916. According to that technique, a coil having an enlarged portion is mated with a pusher having a keyway adapted to receive the enlarged portion of the coil in an interlocking relationship. The joint between the pusher and the coil is covered by a coaxial member. The coaxial member is movable by sliding the member axially. As the coaxial member is moved away from the junction where the coil's member engages the keyway of the pusher, the coil is freed from the catheter assembly and the pusher may then be removed.

Another IDC device for placement of coils is shown in U.S. Pat. No. 5,234,437. This device includes a coil having a helical portion at least one end and a pusher wire having a distal end that is threaded inside of the helical coil by use of a threaded section on the outside of the pusher. The device operates by engaging the proximal end of the coil with a sleeve and unthreading the pusher from the coil. Once the pusher is free, the sleeve may be used to push the coil out into the targeted treatment area.

U.S. Pat. No. 5,312,415 discloses the use of a catheter having a constricted or feathered end to retain a number of embolic coils on a guidewire for precise placement using a pusher sheath.

Electrolytic coil detachment is disclosed in U.S. Pat. Nos. 5,122,136 and 5,354,295. According to U.S. Pat. No. 5,122,136, the coil is bonded via a metal-to-metal joint to the distal end of the pusher. The pusher and coil are made of dissimilar metals. The coil-carrying pusher is advanced through the catheter to the site and a small electrical current is passed through the pusher-coil assembly. The current causes the joint between the pusher and the coil to be severed via electrolysis. The pusher may then be retracted leaving the detached coil at an exact position within the vessel. Since no significant mechanical force is applied to the coil during electrolytic detachment, highly accurate coil placement is readily achieved. In addition, the electric current may facilitate thrombus formation at the coil site. The only perceived disadvantage of this method is that the electrolytic release of the coil may require a period of time that may inhibit rapid detachment of the coil from the pusher.

Another method of placing an embolic coil is disclosed in U.S. Pat. No. 5,108,407. This patent shows the use of a device in which embolic coils are separated from the distal end of a catheter by the use of heat-releasable adhesive bonds. The coil adheres to the therapeutic device via a mounting connection having a heat sensitive adhesive. Laser energy is transferred through a fiber optic cable which terminates at that connector. The connector becomes warm and releases the adhesive bond between the connector and the coil. Among the drawbacks of this system is that it involves generally complicated laser optic componentry.

There is a need to provide alternative mechanisms for delivering implants, such as embolic coils, that combine accurate positioning capability with rapid implant decoupling response times.

SUMMARY OF THE INVENTION

The present invention provides an occlusive implant delivery assembly having a rapid response detachment mechanism which avoids or minimizes implant position migration during release. The assembly includes an occlusive implant, a pusher or device to carry the implant to the desired location, and a thermally activated decoupling mechanism that decouples the implant from the assembly. The pusher has a distal section and a proximal section. The distal section includes a coupling portion which comprises shape memory material and exhibits different configurations depending on its temperature. The coupling portion interlockingly engages the implant when it is in one of the configurations and releases the implant from interlocking engagement therewith when in another one of the configurations.

With this construction, the implant can be delivered very rapidly without any significant displacement of the implant during release. Generally speaking, the thermally actuated detachment mechanism does not apply any significant force on the implant during release. Another advantageous aspect of the invention is that the simple one-piece construction of the detachment mechanism can be readily manufactured and assembled.

According to a first embodiment of the invention, a body temperature activation system is utilized to activate the coupling portion. With this system, the properties of the shape memory material are selected so that when the coupling portion reaches body temperature via heat transfer from the surrounding tissue and fluids at the delivery site, the coupling portion returns to its original, preset configuration. In order to avoid premature activation (as the implant is guided to the desired site), a biocompatible cooling solution is flushed through the catheter during introduction and placement of the implant. When the implant is in the desired location, the cooling solution is no longer circulated, thereby allowing the coupling portion to heat up to body temperature where it returns to its original, release configuration. Accordingly, the need for auxiliary heating means to activate the release mechanism is eliminated.

In a further embodiment of the invention, an auxiliary electrical heating system is used to heat the coupling mechanism to the desired temperature. In this embodiment, the shape memory material is selected to be triggered for return to its original shape at a temperature above body temperature and preferably above febrile temperatures. With this configuration, the energy input into the coupling portion can be precisely controlled and extremely rapid activation response times achieved.

In operation, the implant delivery assembly is introduced into the body of a mammal via a guide catheter suited for the particular lumen being navigated. When the implant is positioned at the desired site, the coupling portion of the pusher is thermally activated to effect the return of its original, pre-set configuration, which is originally formed to release the implant from interlocking engagement therewith. The coupling portion is thermally activated using body heat or auxiliary electrical means as discussed above. Then, the pusher can be readily removed from the implant without imparting any significant force thereon.

The above is a brief description of some of the features and advantages of the present invention. Other features, advantages and embodiments of the invention will be apparent to those skilled in the art from the following description, accompanying drawings and appended claims.

DETAILED DESCRIPTION OF THE PREFERRED EMBODIMENTS

Figure 1A:
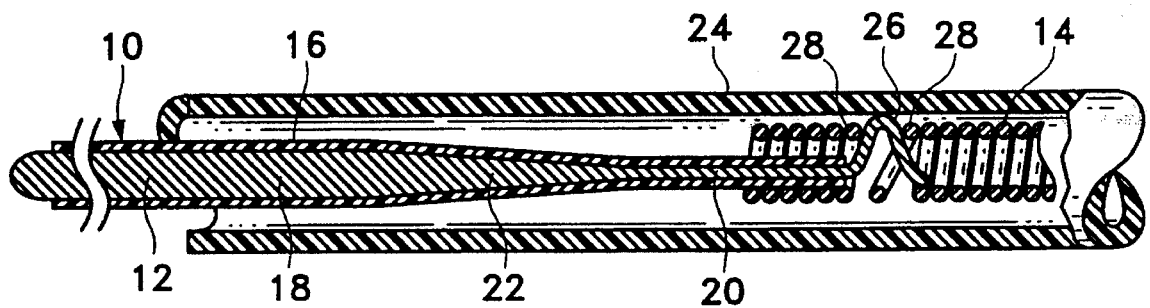
FIG. 1a is a partial sectional view of an implant delivery assembly constructed according to the principles of the present invention showing the assembly in a locked state.

Referring to the drawings in detail, wherein like numerals indicate like elements, an implant delivery assembly 10 for facilitating occlusion of a body conduit in a mammal is shown in accordance with the principles of the present invention. It should be understood, however, that the form of the implant can vary depending, for example, on the body conduit in the vascular, biliary, genitourinary, gastrointestinal and respiratory systems undergoing treatment as would be apparent to one of ordinary skill in the art. Thus, although the illustrated vasoocclusive coil-type implant will be described below for purposes of example, other occlusive implant configurations can be used as well.

Figure 1B:
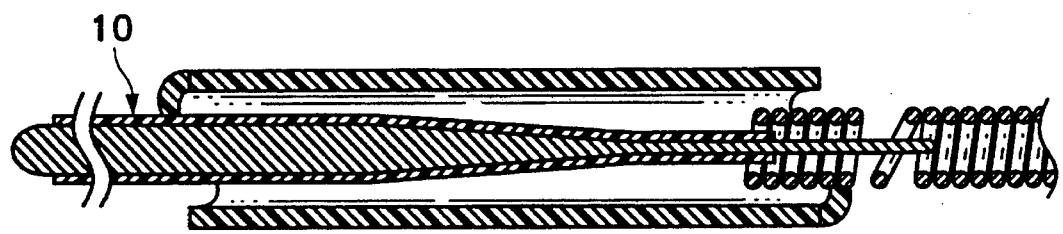
FIG. 1b is a partial sectional view of the implant delivery assembly of FIG. 1a in an unlocked state.

Referring to FIGS. 1a and 1b, assembly 10 generally comprises a pusher or delivery member 12, which is an elongated member, and an implant 14 detachably coupled thereto. According to the present invention, pusher 12, or at least a portion thereof, comprises shape memory material and provides a thermally activated decoupling mechanism as will be described in more detail below. The pusher preferably is insulated by a polymeric sleeve or casing 16 to protect surrounding cells and tissue when the pusher is heat activated. Sleeve 16 can be coated or comprise lubricious material to improve the lubricity of the pusher. This is especially advantageous when the pusher is guided through a catheter.

As shown in FIGS. 1a and 1b, pusher 12 generally comprises a relatively long torqueable proximal section 18 and a relatively short flexible distal section 20 constructed for atraumatic navigation along extremely tortuous vasculature passageways. The large proximal portion facilitates torque transfer, while the small sizing of distal section 20 enhances its flexibility. Tapered section 22 interconnects proximal and distal sections 18 and 20. The pusher also is sized for advancement through or retraction from a suitable catheter as shown in FIGS. 1a and 1b and designated with reference numeral 24. Pusher 12 can be provided with the desired profile by conventional grinding techniques currently used in guidewire manufacture.

As discussed above, pusher 12 comprises shape memory material. Shape memory material is material which exhibits mechanical memory when activated by heat. An example of such material is titanium-nickel (TiNi) alloy, usually referred to as nitinol. Shape memory alloys or materials have a transition temperature that depends on the particular ratio of the metals in the alloy, and/or the effects of annealing and cold working (e.g., grinding during fabrication of the shape memory component). In brief, shape memory material can be (1) formed into a first shape at a temperature above its transition temperature, (2) brought below its transition temperature and, once there, plastically deformed into a second desired shape and (3) returned to its first pre-set form upon reheating above its transition temperature.

According to the present invention, the entire pusher, or at least a portion thereof comprises shape memory material and a portion of the distal section of the pusher is constructed to form the coupling or locking portion. Thus, at least this coupling portion comprises shape memory material. The coupling portion is constructed with an intermediate deformed shape that provides a mechanism for securing the implant to the pusher and a pre-set shape that provides release of the implant as will be described in more detail below.

In manufacturing the delivery assembly shown in the drawings, the general profile of the pusher can be obtained by conventional grinding techniques as discussed above. The pusher is originally formed to a pre-set shape when above the transition temperature where it is austeneric. The pre-set shape is the shape desired for release from the implant. Although a straight release shape is shown as the preferred embodiment for use with coil implant 14, other shapes including curves, angles or multiple configurations may be desired especially in the case of differently configured implants. The pusher preferably is then insulated in polymeric sleeve 16, which is preferably coated with a lubricant compatible with the environment of intended use including the biomaterials of the catheter that may guide the pusher to the desired location in the mammal. Alternatively, sleeve 16 can be made with a lubricous polymer such as polytetrafluoroethene or FEP.

The coupling portion of the distal section is cooled below the transition temperature (where it becomes martensitic) and mechanically deformed to shape the coupling portion into the desired locking configuration. Several possible configurations are shown in the drawings and will be discussed in detail below. Once the locking configuration is obtained, the implant can be secured to the coupling portion of the pusher which generally completes the construction of the implant delivery assembly. When using a one-way shape memory material, the material will maintain its original shape once heated above its transition temperature even when returned to a temperature below the transition temperature unless external forces are again applied.

Figure 3:
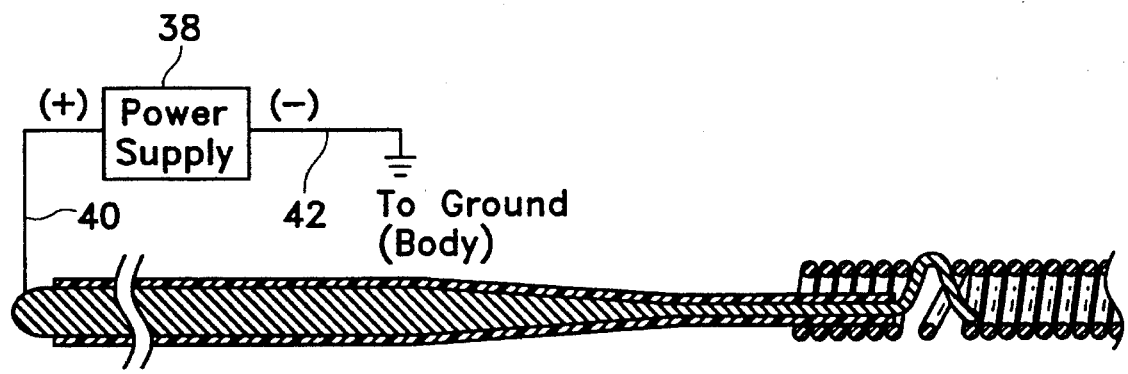
FIG. 3 shows the implant delivery assembly of FIG. 1 incorporating an auxiliary electric supply circuit.

One suitable shape memory alloy is nitinol having about 51–57% nickel by weight and the remaining portion titanium. Other suitable shape memory alloys include copper-zinc-aluminum, copper-aluminim-nickel, copper-zinc-silicon, copper-zinc-tin, gold-cadmium and nickel-cadmium. The transition temperature is selected according to the heating mechanism. When the alloy is activated by body temperature according to a first embodiment shown in FIGS. 1a and 1b, the preferred transition temperature is about 34°–37° C. When the alloy is activated by auxiliary electrical or heating means (as shown in FIGS. 3; 4a, b; and 5a, b), the preferred transition temperature is about 37°–43° C., and preferably is above the febrile temperature range (about 40°–43° C. in human patients) to avoid premature actuation of the mechanism.

Referring to FIGS. 1a and b, a first locking configuration is shown. More specifically, distal section 20 includes coupling portion 26. Portion 26 has a deformed or implant locking configuration generally comprising a U-shaped curve that is sized to extend between and frictionally engage a pair of turns 28 of coil 14. Although coil 28 is shown in the drawings as a uniform diameter helical coil wire, it may have other configurations. It is important, however, that the coil be dimensioned to be able to be advanced through a catheter that is sized to access the desired site.

The coil may be radiopaque, biocompatible metal such as platinum, gold, tungsten, stainless steel or alloys of these metals. Preferably, the coil is platinum, gold or tungsten (or alloys of these metals) so that its location at the desired site may be readily viewed radiographically.

For use in occluding peripheral or neural sites, the coils will typically be made of 0.05 to 0.15 mm diameter platinum wire that is wound to have an inner diameter of 0.15 to 0.96 mm with a minimum pitch (i.e., the windings are close to one another). The length of the wound wire (i.e., the coil) will normally be in the range of 0.5 to 60 cm, and preferably 0.5 to 40 cm. For wires intended for use in vessels with diameters of about 2 mm and smaller, the coil has a preferred length of about 0.5 to 20 cm. The coil can have any shape. For example, it can be formed so that it takes on an essentially linear configuration, in which it may be advanced through the catheter and assume a randomly oriented configuration, such as helical, after it is released from the catheter and in a relaxed state as disclosed in U.S. Pat. No. 4,994,069, which is hereby incorporated herein by reference. Helical metal coils having one or more fibrous elements attached thereto in a sinusoidal wave configuration as disclosed in U.S. Pat. No. 5,226,911 also can be used.

In the example shown in FIGS. 1a and b, a conventional embolic coil is shown with the proximal end of the coil open for receipt of the pusher and a gap formed between windings to receive a portion of the coupling portion. Although the turns of coil 14, between which coupling portion 26 extends, are prestressed so that a gap is formed therebetween, the curve in coupling portion 26 is sufficiently sized to cause the turns to be biased thereagainst when positioned as shown in FIG. 1a. In this manner, coil implant 14 is securely retained on pusher 12.

In contrast, coupling portion 26 preferably has a substantially straight, pre-set shape in this embodiment as shown in FIG. 1b, so that after thermal activation, distal section 20 can be readily withdrawn from coil 14. More specifically, with this preset/release configuration, distal section 20 can be readily withdrawn from coil 14 without exerting any significant force on the coil that would cause any significant coil migration. Of course, the configurations of the coupling portion can vary as would be apparent to one of ordinary skill.

Figure 2A:
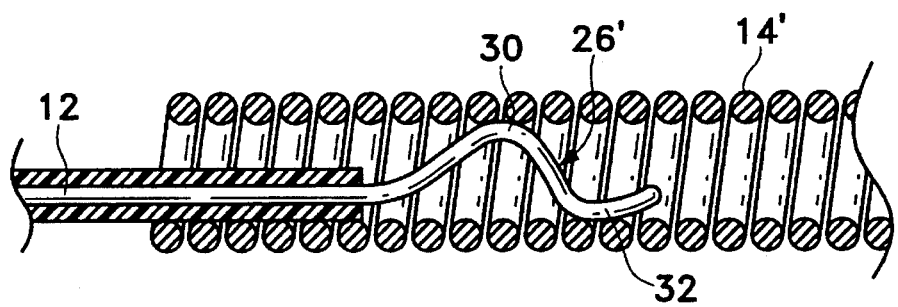
FIG. 2a is a partial sectional view of the implant delivery assembly of FIG. 1a showing another locking configuration.
Figure 2B:
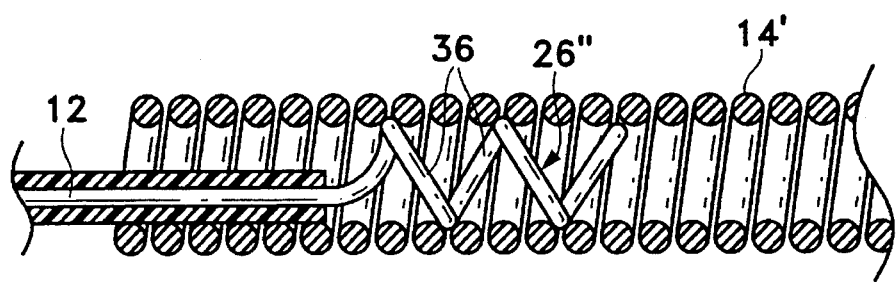
FIG. 2b is a further view of the implant delivery assembly of FIG. 2a in a locked state.

Referring to FIGS. 2a and 2b, additional coupling portion locking configurations are shown. In these embodiments, the coil, designated with reference numeral 14', is formed without the gap between turns as in FIG. 1a. Referring to FIG. 2a, the locking configuration of coupling portion 26' comprises multiple sinusoidal curves. The curves are sized so that each curved segment 30, 32 places a sufficient pressure on the inner circumferential surface of coil 14' to retain coil 14' on the distal section of pusher 12. Although a pair of curves are shown forming the sinusoidal shape in FIG. 2a, other numbers of curves can be used as well.

In a further alternative as shown in FIG. 2b, the locking configuration of coupling portion 26" is helical. The coupling portion windings 36 lodge between windings of coil 14' as shown in FIG. 2a, to generate sufficient bias and retain the coil on pusher 12. The pitch of the coupling portion windings preferably generally corresponds to the pitch of the windings of coil 14'.

In each of these examples, the coupling portion pre-set shape is substantially straight as shown in FIG. 1b and as described above. It also should be understood that other locking configurations can be used without departing from the scope of the invention.

Referring to FIGS. 3; 4a,b; and 5a,b, various electric circuits are shown for heating the coupling portion of the pusher. Referring to FIG. 3, power supply 38 has a first lead 40 coupled to the proximal end of pusher 12 and a second lead 42 for coupling to the skin of the patient. Lead 42 typically is connected to the negative pole of the power supply and a positive electric current of about 0.001 to 2 milliamps at 0.1 to 6 volts is applied to the pusher via lead 40. These volt-amp ranges also apply to the power supply circuits shown in FIGS. 4a,b and 5a,b.

Figure 4A:
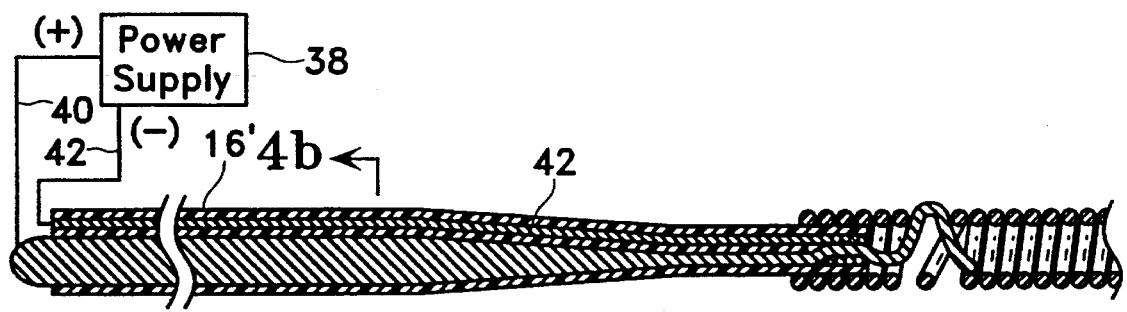
FIG. 4a shows the implant delivery assembly of FIG. 1 incorporating another electric supply circuit.
Figure 4B:
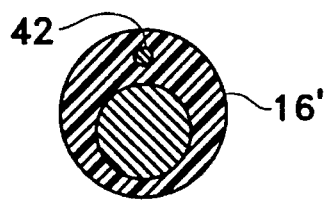
FIG. 4b is sectional view of the delivery system of FIG. 4a taken along line 4b—4b.

Referring to FIGS. 4a and 4b, another configuration for the attachment of the leads to the implant delivery assembly is shown. In this configuration, lead 42 extends through insulation 16', which is a dual lumen extruded polymeric element, and is attached to the pusher adjacent to the coupling portion. The attachment can be formed, for example, by tightly winding lead 42 around the pusher as shown in FIG. 4a and/or soldering or welding lead 42 to the pusher to provide a suitable electrical connection.

Figure 5A:
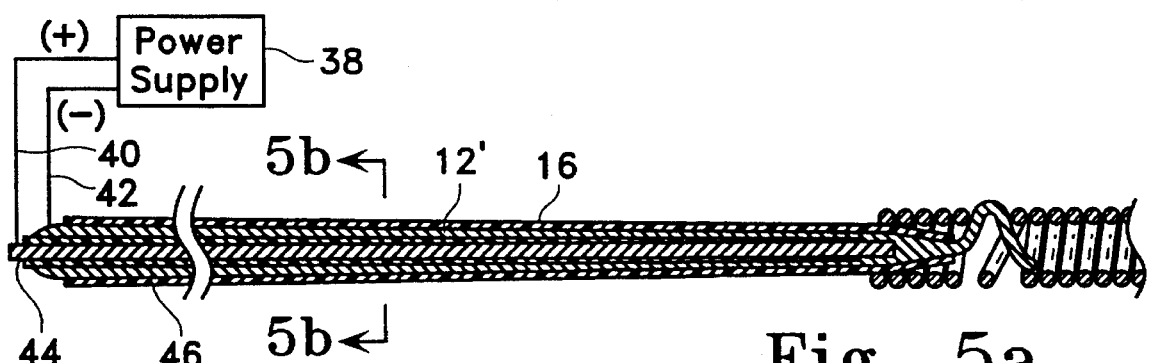
FIG. 5a shows the implant delivery assembly of FIG. 1 with yet another electric supply circuit.
Figure 5B:
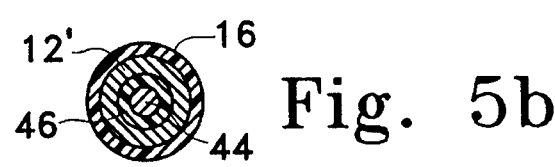
FIG. 5b is a sectional view of the delivery assembly of FIG. 5a taken along line 5b—5b.

A further configuration for the power supply circuit is shown in FIGS. 5a and 5b. In this configuration, lead 42 is coupled to the proximal end of the pusher 12' which is formed as a hypotube. Lead 40 is coupled to conductor 44 which is coaxially positioned within pusher 12'. Tubular insulation sleeve 16 surrounds pusher 12, while tubular insulation sleeve 46 separates pusher 12 from conductor 44. The distal tip of conductor 44 can be in the range of 0.2 to 40 cm from the coupling portion, and preferably is within about 0.2 to 0.5 cm from the coupling portion to provide virtually instantaneous response and, thus, decoupling.

Power source 38 includes conventional controls for controlling current input and input duration as is conventional in the art. It is also contemplated that conventional processing componentry can be coupled to the pusher to control the exact instant of detachment of the implant from the distal section of pusher 12.

Merely to exemplify the operation of the invention, the following example in which an implant delivery assembly constructed as shown in the drawings to deliver an occlusive coil to a vascular site is provided. Implant delivery assembly 10 is delivered through a catheter, e.g., catheter 24 to a selected vascular site. Catheter 24 generally comprises an elongate tubular member having proximal and distal end portions. The catheter is preferably between about 50–300 cm in length, and typically between about 60–200 cm in length. The catheter also is designed for accessing a vessel site at which, for example, vasoocclusion is desired. For example, the vessel site can be within a small diameter vessel having 2–5 mm lumen diameter and accessible by way of a tortuous vessel path which may involve sharp vessel turns and multiple vessel branches. In this case, the catheter preferably has a small diameter, flexible construction with a lumen diameter of less than about 40 mil and preferably between about 8–30 mil. Catheters of this type, which are typically used for accessing deep brain vascular sites, are commercially available.

The catheter is inserted through a vessel lumen (not shown) to the site to be occluded (e.g., an aneurysm, vascular malformation, or arteriovenous fistula). Conventional catheter insertion and navigational procedures involving guidewire and/or flow-directed means may be used to access the site with the catheter. Thus, although not shown, catheter 24 may include a guidewire usable therewith to guide the distal end of the catheter toward the desired or selected occlusion site. Guidewires of this type are commercially available, and generally include an elongate wire having a tapered, wire-wound distal end region which is adapted to be advanced through a tortuous vessel path, with the catheter being moved axially along the advanced guidewire.

Once the distal end of the catheter is positioned at the selected site (its location may be determined by a coating at the distal end of the catheter with a radiopaque material or otherwise affixing such a material to the distal end of the catheter or incorporating such a material into the distal end of the catheter), the catheter is cleared. For example, if a guidewire has been used to position the catheter, it is withdrawn from within the catheter.

Pusher 12 is manipulated forwards and backwards until the desired lie of the coil is obtained. This technique is similar to the procedure used with the Guglielmi Detachable Coil (GDC) described in U.S. Pat. No. 5,122,136 which is hereby incorporated herein by reference. Once coil 14 is in position, the coupling portion can be activated by body heat or auxiliary heating means. When using a body temperature activation system, the properties of the shape memory material are selected so that when the coupling portion reaches body temperature via heat transfer from the surrounding tissue and fluids at the delivery site, the coupling portion returns to its original, pre-set configuration. Preferred transition temperatures are described above. However, in order to avoid premature activation (as the implant is guided to the desired site), a biocompatible solution is flushed through the catheter during introduction and placement of the implant to maintain the implant below the transition temperature. When the implant is in the desired location, the cooling solution is no longer circulated, thereby allowing the coupling portion to heat up to body temperature where it returns to its original, release configuration.

Alternatively, auxiliary heating means such as that illustrated in FIGS. 3; 4a,b; or 5a,b can be used and the coolant circulation step eliminated. In this case, once coil 14 is in the desired position, an electric current is applied to pusher 12, which in this example essentially consists of the shape memory material, by a power source 38. Heat is generated by electric current applied to the pusher in a region upstream to the coupling portion 26 (26, 26") and transferred to coupling portion 26 (26',26"). When the temperature of the coupling portion rises above the transition temperature of the shape memory material (preferred transition temperatures are described above), the heat effects the return of the original, pre-set shape, which is straight in the illustrative embodiments, thereby releasing coil 14 from interlocking engagement from pusher 12. Pusher 12 can then be readily retracted without causing significant migration of the coil, or coils previously positioned at the site and adjacent the last placed coil. The precision and rapid delivery achievable from this mechanism is especially advantageous in neural procedures.

The above is a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. An occlusive implant delivery assembly for occluding a site in a mammal, said assembly comprising an implant and a pusher, said pusher having a distal section and a proximal section, said distal section having a coupling portion comprising thermal memory material and exhibiting different configurations depending on the temperature of said portion, said coupling portion interlockingly engaging said implant when said coupling portion is in a first one of said configurations and disengaging from said implant when in second one of said configurations.

2. The assembly of claim 1 wherein said implant comprises a coil having multiple turns and said distal section has a curved portion that extends between a number of said turns when said coupling portion is in said first configuration.

3. The assembly of claim 1 wherein said implant comprises a coil having an inner surface, said coupling portion having multiple curves, each placing a pressure on a different portion of said inner surface when said coupling portion is said first configuration.

4. The assembly of claim 3 wherein said portions of said inner surface are generally equidistantly spaced in the circumferential direction.

5. The assembly of claim 3 wherein said coupling portion has a sinusoidal shape when in said first configuration.

6. The assembly of claim 1 wherein said implant comprises a coil and when said coupling portion is in said first configuration it has a helical shape with a pitch that generally corresponds to that of said coil.

7. The assembly of claim 1 further including an insulation sleeve, said insulation sleeve encasing said pusher.

8. The assembly of claim 1 further including leads having first portions coupled to said pusher and second portions adapted for coupling to a power source.

9. An occlusive implant delivery assembly for occluding a site in a mammal, said assembly comprising an implant and a pusher, said pusher having a distal section and a proximal section, said distal section having a coupling portion comprising thermal memory material having a transition temperature and exhibiting multiple configurations depending on the temperature of said portion, said coupling portion interlockingly engaging said implant when said coupling portion is in one of said configurations and being disengaged from interlocking engagement with said implant when in a second one of said configurations such that said distal section can be readily removed from said implant, whereby when the temperature of the coupling portion is brought above its transition temperature, the coupling portion reconfigures to said second configuration and releases said implant.

10. A method of placing an implant in a mammal comprising the steps of:

(a) introducing in a mammal, a pusher having a heat activated decoupling mechanism; an occlusive implant detachably coupled to the decoupling mechanism; and (b) applying energy to the decoupling mechanism to effect decoupling the pusher from the implant.

11. The method of claim 10 further including the step of positioning a catheter in the mammal and introducing the pusher in the mammal via the catheter to deliver the implant to the desired location.

12. The method of claim 10 wherein said implant comprises a coil.

13. The method of claim 10 wherein said implant is introduced into the vasculature of the mammal.

14. The method of claim 10 wherein said thermal memory material has a transition temperature in the range of about 34° to 37° C.

15. The method of claim 10 wherein said thermal memory material has a transition temperature in the range of about 37° to 43° C.

16. The method of claim 10 wherein said thermal memory material has a transition temperature in the range of about 40° to 43° C.

17. The assembly of claim 1 wherein said thermal memory material has a transition temperature in the range of about 34° to 37° C.

18. The assembly of claim 1 wherein said thermal memory material has a transition temperature in the range of about 37° to 43° C.

19. The assembly of claim 1 wherein said thermal memory material has a transition temperature in the range of about 40° to 43° C.

20. The assembly of claim 9 wherein said thermal memory material has a transition temperature in the range of about 34° to 37° C.

21. The assembly of claim 9 wherein said thermal memory material has a transition temperature in the range of about 37° to 43° C.

22. The assembly of claim 9 wherein said thermal memory material has a transition temperature in the range of about 40° to 43° C.

23. The assembly of claim 9 wherein said implant comprises a coil.

* * * * *